United States Patent [19]

Eggensperger et al.

[11] 4,178,375

[45] Dec. 11, 1979

[54] PRESERVING AND DISINFECTING METHOD EMPLOYING CERTAIN OXAZINES

[75] Inventors: Heinz Eggensperger, Hamburg; Karl-Heinz Diehl, Norderstedt, both of Fed. Rep. of Germany

[73] Assignee: Sterling Drug Inc., New York, N.Y.

[21] Appl. No.: 934,792

[22] Filed: Aug. 17, 1978

Related U.S. Application Data

[62] Division of Ser. No. 819,245, Jul. 27, 1977, Pat. No. 4,148,905.

[30] Foreign Application Priority Data

Aug. 6, 1976 [DE] Fed. Rep. of Germany ............ 2635389

[51] Int. Cl.² ............................................. A01N 9/22
[52] U.S. Cl. .................................... 424/248.4; 544/88
[58] Field of Search ......................... 424/248.4; 544/88

[56] References Cited

U.S. PATENT DOCUMENTS

| | | | |
|---|---|---|---|
| 2,647,118 | 7/1953 | Hartough et al. | 544/88 |
| 2,831,858 | 4/1958 | de Benneville et al. | 544/88 |

*Primary Examiner*—V. D. Turner
*Attorney, Agent, or Firm*—Frederik W. Stonner; B. Woodrow Wyatt

[57] ABSTRACT

A method for preventing or retarding the growth of bacteria and fungi in a material which comprises treating the material with N,N'-methylenebis-(oxazolidines) and -(tetrahydro-1,3-oxazines), and certain novel N,N'-methylenebis-(oxazolidines).

3 Claims, No Drawings

PRESERVING AND DISINFECTING METHOD EMPLOYING CERTAIN OXAZINES

This is a division, of application Ser. No. 819,245, filed July 27, 1977, now U.S. Pat. No. 4,148,905.

BACKGROUND OF THE INVENTION

1. Field of the Invention

The invention relates to a method for preventing or retarding the growth of bacteria and fungi in materials such as, for example, industrial solutions, emulsions, dispersions and suspensions, which comprises treating such materials with antibacterially and antifungally effective N,N'-methylenebis(oxazolidines) or N,N'-methylenebis-(tetrahydro-1,3-oxazines), and to novel N,N'-methylenebis(oxazolidines).

2. Description of the Prior Art

U.S. Pat. No. 2,647,117 discloses bis(tetrahydro-1,3-oxazino)-methanes of the formula

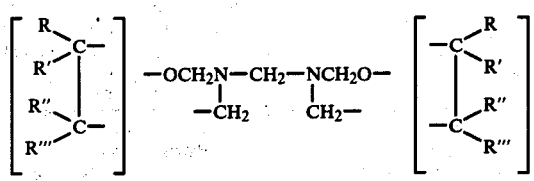

where R, R', R" and R''', inter alia, are hydrogen or alkyl. Specific compounds of the above formula which are disclosed are:

| R | R' | R" | R''' |
|---|---|---|---|
| $CH_3$ | $(CH_3)_3CCH_2$ | H | H |
| $CH_3$ | $CH_3$ | $CH_3$ | H |
| $(CH_3)_2CH$ | $(CH_3)_2CH$ | H | H |

The sole utility disclosed for these compounds is that they have industrial application as emulsifiers.

Rec. trav. chim. 78, 320 (1959) discloses bis(tetrahydro-1,3-oxazin-3-yl)methane. No utility is disclosed for this compound.

Chem. Abstracts 58, 12750b (1963) and J. Org. Chem. 44 (10), 1768, 1771 and 7773 (1976) disclose N,N'-methylenebis(4,4-dimethyloxazolidine). No utility is disclosed for this compound. However, the J. Org. Chem. reference teaches that this compound displays some activity against lymphocytic luekemia.

The trishydroxyalkylhexahydrotriazines, e.g. trishydroxyethylhexahydrotriazine, are well known antimicrobial agents which are prepared by reacting, in a ratio of 1:1, an alkanolamine and formaldehyde, which reactants in a ratio of 1:1.5 yield N,N'-methylenebis(oxazolidines) and -(tetrahydro-1,3-oxazines).

SUMMARY OF THE INVENTION

It has been found that N,N'-methylenebis(oxazolidine), N,N'-methylenebis(tetrahydro-1,3-oxazine) and corresponding ring alkylated derivatives possess excellent antimicrobial, i.e., antibacterial and anti-fungal, activity.

Thus in one aspect of the invention there is provided a method for preventing or retarding the growth of bacteria and fungi in a material susceptible to bacterial and fungal contamination which comprises treating the material with an antibacterially and antifungally effective amount of at least one compound of the formula

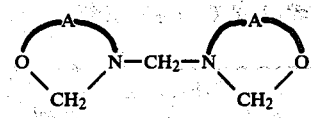

where A is alkylene selected from the group consisting of 1,2-alkanediyl having from 2 to 10 carbon atoms and 1,3-alkanediyl having from 3 to 10 carbon atoms.

In another aspect of the invention there is provided a compound selected from the group consisting of N,N'-methylenebis(oxazoline), N,N'-methylenebis-(5-methyloxazolidine) and N,N'-methylenebis(4-ethyloxazolidine).

The method of the invention is useful for preserving and disinfecting industrial solutions, emulsions, dispersions and suspensions, such as water-based paints, cold lubricating agents, adhesive solutions and dispersions, cosmetic and pharmaceutical products and aqueous formulations such as self-polishing wax emulsions and water circulation systems, e.g., cooling water circulation systems and recycled water systems used in paper manufacture.

DETAILED DESCRIPTION INCLUSIVE OF THE PREFERRED EMBODIMENTS

The compounds employed in the method of the invention can be prepared by reacting an aminoalcohol of the formula $NH_2$—A—OH, where A has the meaning defined hereinabove, with formaldehyde in the ratio of 1:1.5 to 1:2 of aminoalcohol to formaldehyde. The reaction is conveniently carried out by heating a mixture of the aminoalcohol and formaldehyde at a temperature of about 60° for about thirty minutes and subsequent removal of the water formed in the course of the reaction by azeotropic distillation. The product is then purified using standard procedures. If desired, the resulting reaction mixture can be employed directly in the method of the invention without removing the water during the reaction. However, due to the presence of the reaction water in the reaction mixture, rearrangement reactions occur which result in non-defined compounds.

The aminoalcohol starting materials belong to a well-known class of compounds which are readily available or can be readily prepared by well known procedures.

Throughout this specification, the term "1,2-alkanediyl having from 2 to 10 carbon atoms" means 1,2-ethanediyl, 1,2-ethanediyl substituted by from 1 to 4 alkyl substituents wherein the total number of carbon atoms in the combined alkyl substituents does not exceed eight, 1,3-propanediyl and 1,3-propanediyl substituted by from 1 to 6 alkyl substituents wherein the total number of carbon atoms in the combined alkyl substituents does not exceed seven.

The following examples illustrate the preparation of compounds employed in the method of the invention. The structures of the compounds were determined by infrared and nuclear magnetic resonance spectra.

EXAMPLE 1

N,N'-Methylenebis(oxazolidine)

Monoethanolamine (1 mole) was heated in a reaction flask to 60° C. with stirring and 1.5 moles paraformaldehyde was added in portions during 60 minutes. after the addition was completed, stirring at the same temperature was continued for 30 minutes. The reaction water was then distilled off. The resulting residue was distilled to give the title compound as a light colored liquid; b.p.$_{12\ mm}$ = 108°–110° C.; $n_{20}{}^D$ = 1.4890.

| Analysis: | $CH_2O$ | | Amine | |
|---|---|---|---|---|
| | calc'd | found | calc'd | found |
| | 57% | 54.3% | 77.2% | 77.7% |

EXAMPLE 2

N,N'-Methylenebis(5-methyloxazolidine)

1-Amino-2-propanol (1 mole) was heated to 60° and 1.5 moles paraformaldehyde was added during one hour. Stirring was continued for one-half hour and the reaction mixture was cooled to room temperature. Benzene (100 ml.) was added and the reaction water was removed by azeotropic distillation. The benzene was evaporated and the resulting residue was distilled to give 85 g. of the title compound as a colorless liquid; b.p.$_{12\text{-}13\ mm}$ = 112°–116° C. (b.p.$_{36\ mm}$ = 138°–142° C.); $n_{20}{}^D$ = 1.4667.

| Analysis: | $CH_2O$ | | Amine | |
|---|---|---|---|---|
| | calc'd | found | calc'd | found |
| | 48.4% | 46.2% | 80.7% | 78% |

EXAMPLE 3

N,N'-Methylenebis(4,4-dimethyloxazolidine)

2-Amino-2-methyl-1-propanol (1 mole) and 1.5 moles paraformaldehyde were refluxed in benzene. After separation of the reaction water, the solvent was distilled off. The residue was distilled to give the title compound as a colorless liquid; b.p.$_6$ $_{mm}$ = 116°–121° C.; $n_{20}{}^D$ = 1.4653.

| Analysis: | $CH_2O$ | | Amine | |
|---|---|---|---|---|
| | calc'd | found | calc'd | found |
| | 42% | 41.3% | 83.2% | 80.1% |

EXAMPLE 4

N,N'-Methylenebis(4-ethyloxazolidine)

1.5 moles paraformaldehyde was added at 60° C. with stirring to 1 mole of 2-amino-1-butanol. After completion of addition, stirring was continued for one-half hour and the reaction water was removed. The resulting residue was distilled to give the title compound; b.p.$_6$ $_{mm}$ = 128°–129° C.; $n_{20}{}^D$ = 1.4653.

| Analysis: | $CH_2O$ | | Amine | |
|---|---|---|---|---|
| | calc'd | found | calc'd | found |
| | 42% | 41.3% | 83.2% | 80.1% |

EXAMPLE 5

N,N'-Methylenebis(tetrahydro-1,3-oxazine)

1.5 moles paraformaldehyde was added during one hour to 1 mole 3-amino-1-propanol at 60° C. Benzene was added and the reaction water was removed by azeotropic distillation. The resulting residue was distilled to give the title compound; b.p.$_{12\ mm}$ = 131°–132° C.; $n_{20}{}^D$ = 1.4846.

| Analysis: | $CH_2O$ | | Amine | |
|---|---|---|---|---|
| | calc'd | found | calc'd | found |
| | 48.4% | 47.5% | 80.7% | 80.9% |

The antimicrobial activity of the compounds employed in the method of the invention were determined in a tube dilution test in accordance with the Richtlinien für die Prüfung chemischer Desinfektionsmittel der Deutschen Gesellschaft für Hygiene und Mikrobiologie (3. Auflage, 1972). The minimum inhibitory concentrations (MIC) of the compounds of Examples 1 to 5 with respect to several organisms are tabulated in Table 1.

Table 1

| Example No. | MIC (Weight-percent of compound) Microorganism (see list below) | | | | | | | |
|---|---|---|---|---|---|---|---|---|
| | a | b | c | d | e | f | g | h |
| 1 | 0.01 | 0.01 | 0.02 | 0.02 | 0.02 | 0.02 | 0.04 | 0.04 |
| 2 | 0.01 | 0.02 | 0.02 | .02 | 0.02 | 0.06 | 0.06 | 0.125 |
| 3 | 0.01 | 0.03 | 0.03 | .03 | 0.02 | 0.03 | 0.125 | 0.125 |
| 4 | 0.01 | 0.01 | 0.03 | .01 | 0.01 | 0.07 | 0.1 | 0.125 |
| 5 | 0.02 | 0.03 | 0.03 | .03 | 0.02 | 0.03 | 0.06 | 0.125 | a. *Staphylococcus aureus*  
b. *Escherichia coli*  
c. *Pseudomonas aeruginosa*  
d. *Proteus vulgaris*  
e. *Bacillus subtilis*  
f. *Aspergillus niger*  
g. *Penicillium glaucum*  
h. *Candida albicans*

The efficacy of the method of the invention was demonstrated in a procedure designed to simulate actual use conditions. The procedure was as follows: Portions of 50 ml. of aqueous cooling-lubricant dilution of standard concentration (normally 4%) were prepared. A test sample was prepared for each compound to be tested by addition of the compound in appropriate use concentration to the cooling-lubricant dilution. These test samples were challenged twice weekly with 1%(0.5 ml pro 50 ml) inoculum. The titer of this inoculum was at least $10^6$ microorganisms per ml.

At the beginning of the test 1 g cast-iron chips (GU 21) was added to each test sample. To simulate actual use conditions, the cooling-lubricant dilutions were agitated during the day in 200 ml Erlenmeyer flasks in a shaker. The flasks were not shaken at night. The flasks were not stoppered to insure gas exchange. Losses of the cooling-lubricant dilution due to evaporation and sampling were made up once a week with water of 20° hardness.

Twice per week, immediately prior to a new inoculation, streaking on dextrose-agar plates was carried out. The plates were incubated at 35° C. for testing of bacteria and at 22° C. for testing of fungi; readings were made after 36 and 72 hours respectively. Growth on the plates was rated semiquantitatively from negative to positive to 3-fold positive. Cessation of the preserving action is demonstrated by massive growth, i.e., 3-fold positive growth.

The inoculum consisted of a cooling-lubricant dilution which was inoculated once a week with plate cultivated microorganisms as follows:

| Bacteria | |
|---|---|
| *Escherichia coli* | Yeast and fungi: |
| *Pseudomonas aeruginesa* | Candida spec. |
| *Proteus vulgaris* | Rhodotorula spec. |

| Bacteria | |
|---|---|
| Enterobacter aerogenes | Aspergillus spec. |
| | Fusarium oxysporum |
| | Cephalosporum spec. |

The inoculum so prepared was aerated in a 35° C. water bath in inverted wash bottles in a day-night cycle. Once per week 20% of the total inoculum was discarded and made up with freshly prepared cooling-lubricant dilution to insure a concentration of microorganisms in excess of $10^6$ per ml and to avoid selective cultivation of any one microorganism.

The compounds of Examples 1, 2, 3 and 5 and the known antimicrobial agent, trishydroxyethylhexahydrotriazine (hereafter THT), were tested in the above-described test procedure. The results obtained are tabulated in Table 2.

Table 2

| Compound | Concentration (Wt. %) | Medium[a] | Days elapsed until growth | | | |
|---|---|---|---|---|---|---|
| | | | − | + | ++ | +++ |
| Ex. 1 | 0.15 | Dromus B (4% in $H_2O$) | >19 | | | |
| Ex. 2 | 0.15 | Dromus B (4% in $H_2O$) | >46 | | | |
| Ex. 5 | 0.15 | Dromus B (4% in $H_2O$) | >46 | | | |
| THT | 0.15 | Dromus B (4% in $H_2O$) | 7 | 15 | | 19 |
| Ex. 1 | 0.15 | Addix SF (4% in $H_2O$) | 35 | 38 | | 42 |
| Ex. 2 | 0.15 | Addix SF (4% in $H_2O$) | 38 | 42 | | 46 |
| Ex. 3 | 0.15 | Addix SF (4% in $H_2O$) | 23 | 27 | | 30 |
| Ex. 5 | 0.15 | Addix SF (4% in $H_2O$) | >46 | | | |
| THT | 0.15 | Addix SF (4% in $H_2O$) | 15 | | 18 | 21 |
| Ex. 1 | 0.15 | Oemeta (4% in $H_2O$) | >46 | | | |
| Ex. 2 | 0.15 | Oemeta (4% in $H_2O$) | 30 | 34 | | 38 |
| Ex. 3 | 0.15 | Oemeta (4% in $H_2O$) | >50 | | | |
| Ex. 5 | 0.15 | Oemeta (4% in $H_2O$) | >46 | | | |
| THT | 0.15 | Oemeta (4% in $H_2O$) | 10 | 15 | | 18 |

[a]Dromus B (Trademark) - mineral oil base$^a$ cooling-lubricant
Addix SF (Trademark) - synthetic cooling-lubricant
Oemeta 59 - mineral oil base$^a$ cooling-lubricant The above results demonostrate the excellent antimicrobial activity of the compounds of Examples 1, 2, 3 and 5 and their superiority as antimicrobial agents over the known antimicrobial agent, trishydroxyethylhexahydrotriazine, which is prepared from monoethanolamine and formaldehyde in a manner analagous to the preparation of the compound of Example 1 but where the ethanolamine and formaldehyde are reacted in a ratio of 1:1.

In practicing the method of the invention the compounds can be prepared for use by mixing or dissolving in a suitable liquid carrier, e.g., as solutions in a solvent such as but not limited to water and alcohols.

The amount of the compounds or mixtures thereof to be incorporated in the material to be preserved and disinfected by the method of the invention will depend on various factors such as the nature of the material to be protected, and can readily be determined by one having ordinary skill in the art. Generally an amount will be incorporated which results in a concentration in the material to be protected of from about 0.1 to about 4 percent by weight.

We claim:

1. A method for preventing or retarding the growth of bacteria and fungi in a material susceptible to bacterial and fungal contamination which comprises treating the inanimate material with an antibacterially and antifungally effective amount of a compound of the formula

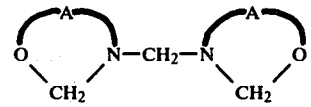

where A is 1,3-alkanediyl having from 3 to 10 carbon atoms.

2. A method according to claim 1 wherein A is 1,3-alkanediyl having from 3 to 5 carbon atoms.

3. A method according to claim 2 where the compound is N,N'-methylenebis(tetrahydro-1,3-oxazine).

UNITED STATES PATENT AND TRADEMARK OFFICE
CERTIFICATE OF CORRECTION

PATENT NO. : 4,178,375
DATED : December 11, 1979
INVENTOR(S) : Heinz Eggensperger and Karl-Heinz Diehl It is certified that error appears in the above-identified patent and that said Letters Patent are hereby corrected as shown below:

Column 1, line 50, "luekemia" should read -- leukemia --.

Column 2, line 14, "methylenebis(oxazoline)" should read -- methylenebis(oxazolidine) --.

Column 6, Claim 1, line 36, "inanimate" should be deleted.

Signed and Sealed this

First Day of April 1980

[SEAL]

Attest:

SIDNEY A. DIAMOND

Attesting Officer

Commissioner of Patents and Trademarks